United States Patent [19]

Matsuo et al.

[11] Patent Number: 5,340,920
[45] Date of Patent: Aug. 23, 1994

[54] PHYSIOLOGICALLY ACTIVE PORCINE PEPTIDE (CNP-53)

[75] Inventors: Hisayuki Matsuo, 5-15-141, 5-chome, Onoharahigashi, Minoo-shi, Osaka; Kenji Kangawa, Miyazaki; Naoto Minamino, Osaka, all of Japan

[73] Assignee: Hisayuki Matsuo, Minoo, Japan

[21] Appl. No.: 728,221

[22] Filed: Jul. 12, 1991

[30] Foreign Application Priority Data

Jul. 13, 1990 [JP] Japan .................. 1-186582

[51] Int. Cl.⁵ .................. C07K 7/00; A61K 37/00; A61K 37/02
[52] U.S. Cl. .................. 530/324
[58] Field of Search .................. 530/324; 514/12

[56] References Cited

U.S. PATENT DOCUMENTS 4,904,763 2/1990 Matsuo et al. .................. 530/324
5,114,923 5/1992 Seilhamer et al. .................. 514/12

OTHER PUBLICATIONS

Tawaragi et al.; "Biochemical and Biophysical Research Communications"; Academic Press Inc: Oct. 30, 1990 pp. 627–632.
Sudoh et al.; "Biochemical and Biophysical Research Communications"; Academic Press, Inc.; Apr. 30, 1990; pp. 863–870.
Minamino et al.; "Biochemical and Biophysical Research Communications"; Academic Press Inc.; Nov. 30, 1988; pp. 402–409.
Minamino et al.; "Biochemical and Biophysical Research Communications"; Academic Press Inc.; Jul. 31, 1990; pp. 973–979.
Tawaragi et al.; "Biochemical and Biophysical Research Communications"; Academic Press Inc.; Oct. 30, 1990; pp. 627–632.

*Primary Examiner*—Merrell C. Cashion, Jr.
*Assistant Examiner*—Carol A. Salata
*Attorney, Agent, or Firm*—Cushman, Darby & Cushman

[57] ABSTRACT

A peptide composed of 53 amino acid residues represented by the following amino acid sequence: (see SEQ ID NO: 1)

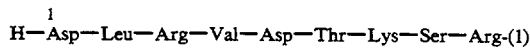
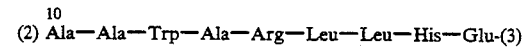
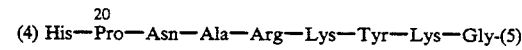
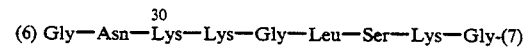
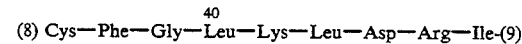
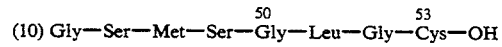

and derivatives thereof represented by the following amino acid sequence: (see SEQ ID NO: 2)

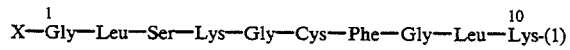
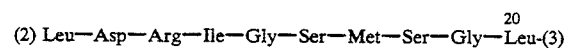
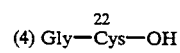

wherein X is as shown in the specification, are disclosed.

These polypeptides are novel and have natriuretic and hypotensive actions.

2 Claims, 7 Drawing Sheets

```
1                   5                          10                       15
Asp-Leu-Arg-Val-Asp-Thr-Lys-Ser-Arg-Ala-Ala-Trp-ala-Arg-Leu-Leu-His-
             20                       25                     30                      35
Glu-His-Pro-Asn-Ala-Arg-Lys-Tyr-Lys-Gly-Gly-Asn-Lys-Lys-Gly-Leu-Ser-Lys-
                                                             1
                                                             Gly-Leu-Ser-Lys-
                              40                      45
Gly-Cys-Phe-Gly-Leu-Lys-Leu-Asp-Arg-Ile-Gly-Ser-Met-Ser-Gly-Leu-Gly-Cys  : CNP-53
                                                                      22
Gly-Cys-Phe-Gly-Leu-Lys-Leu-Asp-Arg-Ile-Gly-Ser-Met-Ser-Gly-Leu-Gly-Cys  : CNP-22
```

Fig. 6

```
-126  CGCAGCCACTGGGACTCGGCCCGCACCGAGCCCGGCCAGTCTGCTCCGCTCGCTTGCCAG                              -64
 -63  TCTGCCGCCCGGCCCCGTGCACCTCTCTGCCGCCGATCTGCGCCCCTCCACCCACAGGCACC                            -1
   1  Met His Leu Ser Gln Leu Leu Ala Cys Ala Leu Leu Thr Leu Leu                              48
      ATG CAC CTC TCC CAG CTG CTG GCT TGC GCT CTG CTC ACG CTC CTC
       1                                                        16
  49  Ser Leu Arg Pro Ser Glu Ala Lys Pro Gly Ala Pro Pro Lys Val Pro                         96
      TCG CTC CGG CCC TCC GAA GCC AAG CCC GGA GCG CCG CCC AAG GTC CCT
      17                                                            32
  97  Arg Thr Pro Pro Gly Glu Val Ala Glu Pro Gln Ala Ala Gly Gly                            144
      CGA ACT CCG CCA GGG GAG GTG GCC GAG CCC CAG GCT GCG GGC GGC
      33                                                        48
 145  Gly Gln Lys Lys Gly Asp Lys Gly Gly Gly Ala Asn Leu                                    192
      GGT CAG AAG AAG GGC GAC AAG GGT GGC GGC GCC AAC CTC
      49                                                 64
 193  Lys Gly Asp Arg Ser Arg Leu Leu Arg Asp Leu Arg Val Asp Thr Lys                        240
      AAG GGC GAC CGG TCT CGA CTC CTC CGG GAC CTG CGC GTG GAC ACC AAG
      65                                                            80
 241  Ser Arg Ala Ala Trp Ala Arg Leu Leu His Glu His Pro Asn Ala Arg                        288
      TCT CGG GCG GCG TGG GCC CGC CTT CTG CAC GAG CAC CCC AAC GCG CGC
      81                                                            96
 289  Lys Tyr Lys Gly Gly Asn Lys Lys Gly Leu Ser Lys Gly Cys Phe Gly                        336
      AAA TAC AAA GGA AAC AAG AAG GGT TTG TCC AAG GGC TGC TTC GGC
      97                                                         112
 337  Leu Lys Leu Asp Arg Ile Gly Asp Cys Gly Leu Gly Cys *                                  384
      CTC AAA CTG GAC CGG ATC GGC GAC TGC GGA CTG TGT TAG TGC
     113                                             126
 385  GGCGACCCCTGGGGCGGGTGAG  407
```

PHYSIOLOGICALLY ACTIVE PORCINE PEPTIDE (CNP-53)

BACKGROUND OF THE INVENTION

This invention relates to novel physiologically active porcine peptides of the CNP family (C-type natriuretic peptides). More particularly, the invention relates to a peptide composed of 53 amino acid residues and derivatives thereof.

Peptides assignable to two different peptide families that are named "atrial natriuretic peptide (ANP)" and "brain natriuretic peptide (BNP)" have recently been discovered from mammalian atria and brains as hormones or nerve transmitters that regulate the homeostatic balance of body fluid volume and blood pressure in vivo. The structures of those peptides, the meebanism of their biosynthesis, as well as their physiological actions have also been unravelied.

The first clue to the discovery of ANP was reported by de Bold et al. in 1981. Finding that significant diuresis occurred when a rat's atrial crude extract was injected intravenously into another rat, de Bold et al. reported the existence of a natriuresis promoting factor in the atrium (de Bold, A. J. et al., Life Sci., 28, 89, 1981). Kangawa et al. later isolated that factor from human atrium, unravelled its structure and named it "atrial natriuretic peptide (ANP)" (Kangawa, K. et al., Bioahem. Biophys. Res. Commun., 118, 131, 1984; Kangawa, K. et al., Nature, 313, 397, 1985). It has been foijrid that litiman ANP (hANP) as it occurs in the atrium is classified into three types, α-, β- and γ-types, according to the molecular weight; α-type hANP (α-hANP) is a single-stranded peptide that consists of 28 amino acids having a single S-S bond in the molecule; β-type hANP (β-hANP) is an antiparallel dimer having an S-S bond formed between the molecules of α-hANP; and γ-type hANP (Y-hANP) is a high-molecular weight protein composed of 126 amino acids, with α-hANP being contained in the C-terminal portion. Further, cDNA for hANP has been isolated and the routes of biosynthesis of α-, β- and γ-hANP have been identified on the basis of analysis of that cDNA, leading to the conclusion that each of those three types of hANP is biosynthesized from a common precursor protein (Oikawa, S. et al., Nature, 309, 724, 1984).

It is already known that among the three types of hANP, α-hANP is chiefly secreted into blood.

Ever since the structure of hANP was first unravelled, the structures of ANPs derived from other mammals have also been studied.

And, today, the following knowledge is available: ANPs have similar amino acid sequences over a broad spectrum of mammals ranging from rodents to humans; α-type ANP (α-ANP) has the same amino acid sequence in higher mammals including humans, dogs and pigs; and α-type ANPs derived from rats and rabbits have entirely the same amino acid sequence as α-hANP except that the methionine residue in position 12 is replaced by an isoleucine residue (Oikawa, S. et al., Biochem. Biophys. Res. Commun., 132, 892, 1985; Forssmann, W. G. et al., Anat. Embryol., 168, 307, 1983).

The first ANP isolate was obtained from the atrium but later studies involving the preparation of anti-ANP antibodies and examination of their distribution in vivo have shown that ANP also occurs in the brain as well as in the atrium. Since ANP-containing neurons have been reported to occur in the hypothalamus and pontine tegmentum of the brain (Cantin, M. et al., Histochemistry, 80, 113, 1984; Saper, C. B. et al., Science, 227, 1047, 1985), it is speculated today that ANP may also work in the brain as a nerve transmitter that participates in the regulation of the cardiovascular system.

The physiological actions of ANP are diverse and are not limited to a marked natriuretic action alone; it has recently been found that it is capable of not only lowering the blood pressure but also suppressing the production of aldosterone from the adrenal cortex. It is therefore clear today that ANP as it is secreted from the atrium into blood not only works as a hormone that regulates the homeostatic balance of body fluid volume and blood pressure but that in the brain it also works as a nerve transmitter for the nerve system to regulate the homeostatic balance of body fluid volume and blood pressure.

Brain natriuretic peptide (BNP) was first isolated from porcine brain and identified by Sudoh et al. in 1988 (Sudoh, T. et al., Nature, 332, 78, 1988). The first BNP isolate (pBNP-26) is a peptide that consists of 26 amino acid residues having a single S-S bond in the molecule and although it is similar to ANP in structure, i.e., in terms of primary amino acid sequence and the mode of S-S binding (producing a ring structure composed of 17 amino acid residues), BNP is clearly distinguishable from ANP. As in the case of ANP, natriuretic and hypotensive actions have been verified for BNP, which has therefore been named "brain natriuretic peptide (BNP)". At a later time, pBNP-32 composed of 32 amino acid residues having 6 amino acids attached to the N-terminus of pBNP-26 was isolated from porcine brain (Sudoh, T. et al., Biochem. Biophys. Res. Commun., 155, 726, 1988); from porcine atrium, a peptide named "γ-BNP" which was composed of 106 amino acids was also isolated and identified (Minamino, N. et al., Bioahem, Bioshys. Res. Commun., 157, 402, 1988).

On the basis of these results, it has been found that the peptides of the BNP family are biosynthesized from precursors that are entirely different from ANP. Further, as of today, the eDNAs of human and rat BNPs have been isolated and the structures of precursors for those BNPs have also become clear (Sudoh, T. et al., Biochem. Biophys. Res. Commun., 159, 1427, 1989; Kojima, M. et al., Biochem. Biophys. Res. Commun., 159, 1420, 1989).

As already mentioned, BNP was first isolated from the brain. It was later found that BNP was present in porcine brain in an amount ten times as much as ANP and that like ANP, BNP also occurred in the atrium (though in an amount of only 2–3% of ANP) to be secreted into blood (Minamino, N. et al., Biochem. Biophys. Res. Commun., 155, 740, 1988; Aburaya, M. et al., Bioahem. Biophys. Res. Commun., 165, 872, 1989). From these facts, it was found that like ANP, BNP worked as a nerve transmitter in the brain and also worked as a hormone to be secreted from the atrium into blood, in either case helping regulate the homeostatic balance of body fluid volume and blood pressure.

In short, the following observations have been obtained to date: at least two obviously different families (ANP family and BNP family) of natriuretic peptides occur in mammals; peptides of these families are not only secreted from the atrium into blood and work as hormones that regulate the homeostatic balance of body fluid volume and blood pressure; they are also biosynthesized in the brain, where they work as nerve transmitters for the nerve system to regulate the homeostatic balance of body fluid volume and blood pressure.

As exemplified by natriuretic peptide, not a single peptide but a plurality of peptides can participate in the regulation of a certain physiological action in vivo (e.g. homeostasis of body fluid volume and blood pressure) and opioid peptide, tachykinin and endothelin have so far been recognized as other examples of such peptides. It has been known that three different families exist for each of these peptides (Hollt, V., Trend Neuro Sci., 6, 24, 1983; Nakanishi, S., Physiol. Review, 67, 1117, 1987; Inoue, A. et al., Proc. Natl. Acad. Sci., U.S.A., 86, 2863, 1989). This had increased the possibility that aside from the natriuretic peptides so far been known to be assignable to ANP and BNP families, peptides that could be classified into a third family might exist. In this regard, the present inventors very recently succeeded in isolating and identifying a novel peptide of a third family of natriuretic peptides from porcine brain and named it "CNP (C-type natriuretic peptide)" (which is hereinafter abbreviated as "CNP-22"). CNP-22 is a peptide composed of 22 amino acid residues and, like ANP and BNP, it forms a ring structure having a single S-S bond in the molecule. As in the case of ANP and BNP, the ring structure is composed of 17 amino acid residues and the primary amino acid sequence forming this ring structure in CNP-22 is highly homologous to that in α-ANP and BNP-32. However, the C-terminal portion of CNP-22 has a largely different structure than in ANP and BNP. Stated more specifically, the C-terminal portions of ANP and BNP have a "tail" structure in which a few additional amino acid residues are attached to the cysteine residue forming the ring structure, whereas the C-terminus of CNP-22 is a cysteine residue at position 22, with no "tail" structure being present. From these facts, it has been found that in spite of its structural similarity to ANP or BNP, CNP-22 is a peptide that belongs to an obviously different family of natriuretic peptides. Further, it has been verified that when administered to rats, CNP-22 exhibits natriuretic and hypotensive actions as in the case of ANP and BNP; it has therefore been found that CNP-22 is a new peptide assignable to a third family of natriuretic peptides in vivo (Japanese Patent Application No. 105047/1990). However, CNP-22 occurs in such smaller amounts in the brain than ANP and BNP that as of today no detailed information has been obtained with respect to the mechanism behind the biosynthesis of CNP-22, its distribution in vivo and physiological actions.

SUMMARY OF THE INVENTION

The present invention has been accomplished under these circumstances and has as an object providing a novel peptide that can be classified as CNP (a third family of natriuretic peptides in mammals) and that is different from the previously isolated and identified CNP-22. An isolate of this novel peptide would help identify the mechanism of CNP biosynthesis, its distribution in vivo and its physiological actions.

BRIEF DESCRIPTION OF THE DRAWINGS

FIG. 3a shows the elution profile of a process in which elution fraction Nos. 111–113 on CM-52 chromatography shown in FIG. 2 were subjected to immunoaffinity chromatography using anti-α-ANP IgG and the peptide fractions adsorbed on the column 60 were further purified on a Hi-pore RP-318 column; and FIG. 3b shows the elution profile obtained when the peptide fraction eluting at the position indicated by an arrow in FIG. 3a, was further purified on a 219 TP54 diphenyl column;

DETAILED DESCRIPTION OF THE INVENTION

Noting that CNP-22 which was previously isolated and identified from porcine brain had an obviously different structure than peptides of the ANP and BNP families, the present inventors prepared an antibody that specifically recognized the structure of CNP-22 (i.e., an antibody that recognized the structure of CNP-22 but did not recognize the structure of ANP or BNP) and planned a project for isolating a novel peptide of the CNP family from porcine brain using as an indicator the performance of a radio-immunoassay (RIA) system that employed the prepared specific antibody.

The present inventors first prepared an anti-CNP-22 antiserum using a chemically synthesized CNP-22 and constructed an RIA system using the antibody. The RIA system was capable of detecting CNP-22 in amounts of the fmol order per assay tube and had extremely small levels of crossreactivity with α-ANP and BNP-26. In the next step, porcine brain was homogenated in glacial acetic acid and the resulting crude extracted fractions of peptide were purified, with the result of RIA used as an indicator, by combinations of various techniques conventionally used in peptide purification. As a result, peptide fractions having molecular weights of ca. 4000–5000 could finally be purified to a homogeneous and pure peptide that showed immunoreactivity with an anti-CNP-22 antiserum as shown in FIG. 3b.

Figure 4A:
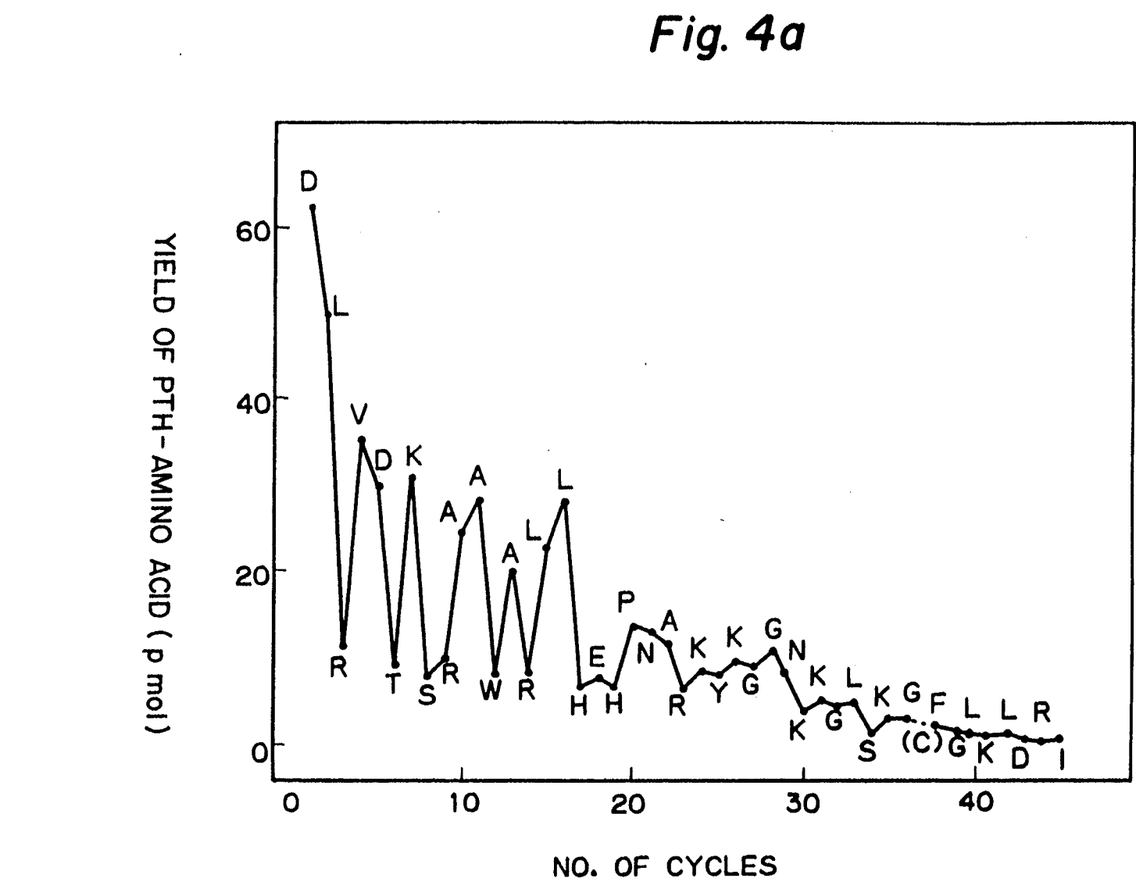
FIG. 4a and FIG. 4b are graphs showing the yield of PTH-amino acid that is produced at successive cycles of the Edman degradation of CNP-53, as well as the amino acid sequence of that PTH-amino acid.
Figure 4B:
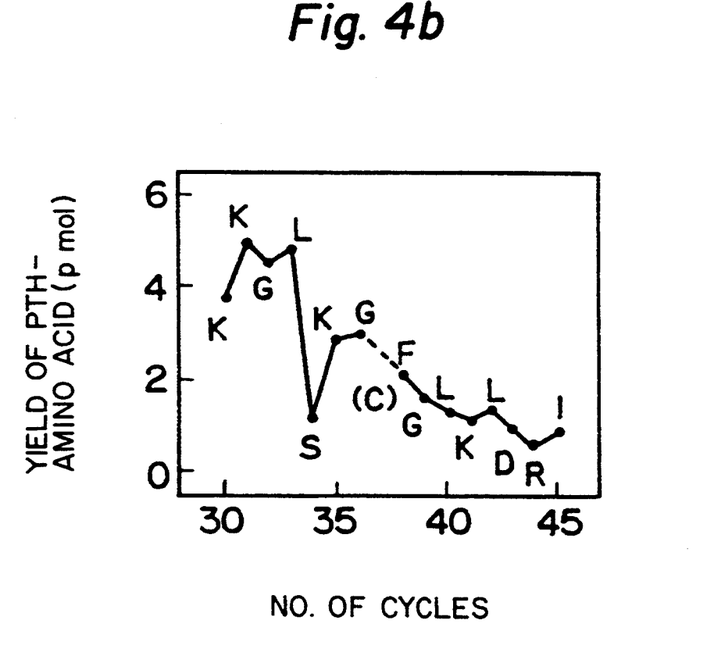

The structure of the thus obtained peptide was determined by the following procedure. First, the primary amino acid sequence of the peptide was analyzed by the Edman method and, as shown in FIG. 4a, the PTH (phenylthiohydantoin)-amino acid that was produced by Edman degradation could be detected and identified up to 45 cycles. Thus, the primary amino acid sequence of the peptide could be determined up to position 45 from the N-terminus. In FIG. 4a amino acids are denoted by one-letter representation and FIG. 4b shows enlarged at a magnification of 4 the yield of PTH-amino acid at 30–45 cycles of the Edman degradation of CNP-53. Since the PTH-amino acid at cycle 37 was not detectable, the present inventors identified this amino acid as cysteine residue (Cys). In the analysis described above, PTH-amino acid was detectable but unidentifiable beyond 45 cycles.

In the next step, the present inventors concluded that the C-terminal structure of the peptide under consideration was identical to CNP-22 in view of the following facts. First, the primary amino acid sequence of the peptide at the N-terminus was compared with CNP-22; as a result, it was found that the primary amino acid sequence from positions 32 to 45 of the peptide was completely identical to the primary amino acid sequence of CNP-22 up to position 14 from the N-terminus. Second, the isolated peptide was measured for its chick rectum relaxant activity and it was found to exhibit comparable activity to CNP-22. As is already known, in order for this biological activity to develop, a ring structure composed of 17 amino acid residues based on the formation of an intramolecular S-S bond in Cys residue is essential; therefore, this ring structure must at least be present in the C-terminal structure of the peptide isolated in accordance with the present invention. Furthermore, the fact that the peptide of the present invention is comparable to CNP-22 in immuno-reactivity per molecule with an anti-CNP-22 antiserum can be explained satisfactorily by assuming that said peptide is composed of 53 amino acid residues with CNP-22 being contained at the C-terminus.

Figure 6:
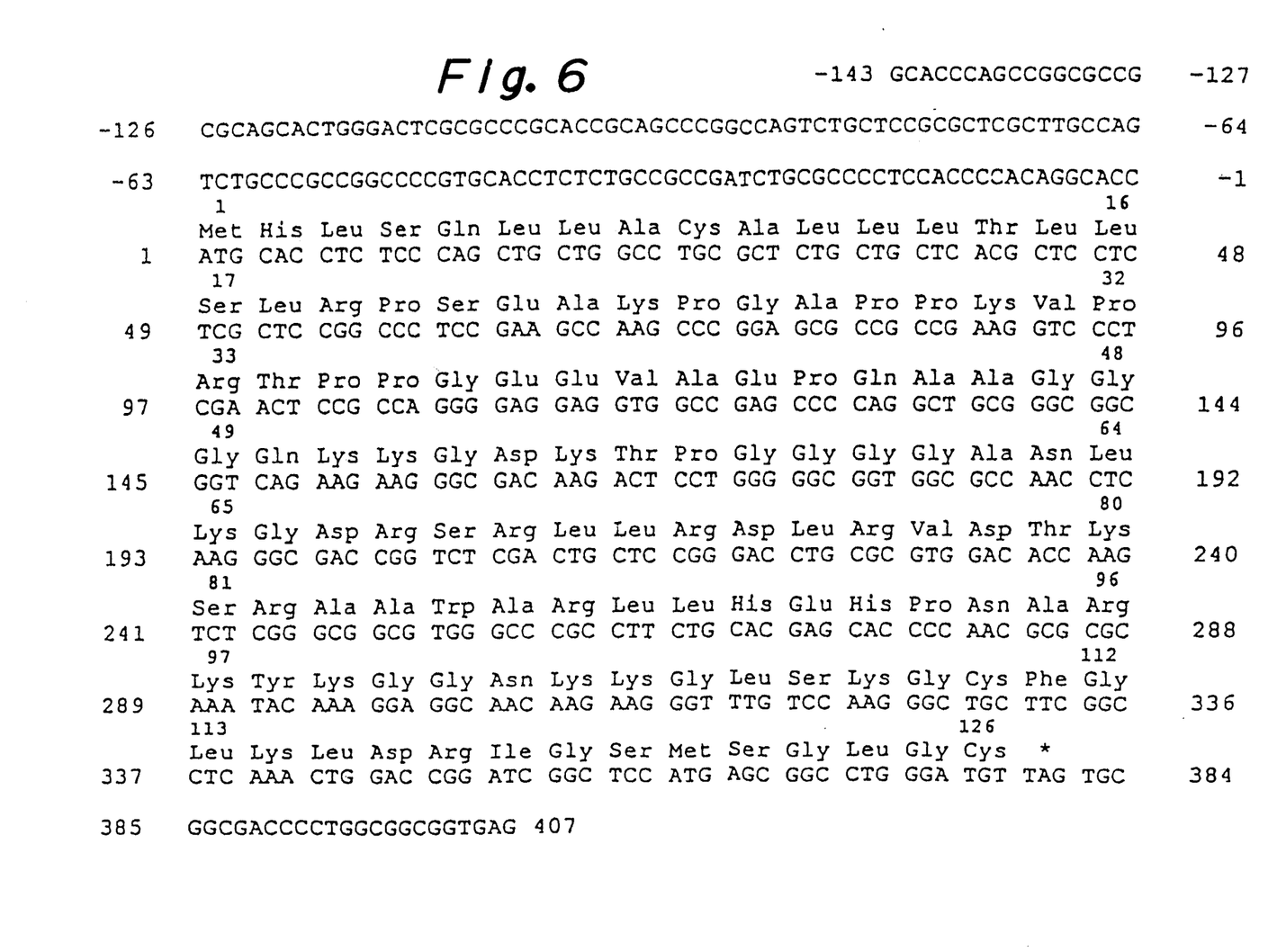
FIG. 6 is a chart showing the seqlkence of a cDNA coding for a CNP-53 (see SEQ ID NO. 1) containing precursor.

The sequence of 8 amino acids at the C-terminus of CNP-53 that could not be analyzed by the Edman method was verified by cloning a cDNA that coded for CNP-53 (see FIG. 6). Details of this cloning are given in the specification of the commonly assigned application which was filed on the same date as this application.

On the basis of these facts, the present inventors finally concluded that the peptide isolated in accordance with the present invention was a novel peptide represented by the following primary amino acid sequence:

```
       1
H—Asp—Leu—Arg—Val—Asp—Thr—Lys—Ser—Arg-(1)

10
(2) Ala—Ala—Trp—Ala—Arg—Leu—Leu—His—Glu-(3)

20
(4) His—Pro—Asn—Ala—Arg—Lys—Tyr—Lys—Gly-(5)

30
(6) Gly—Asn—Lys—Lys—Gly—Leu—Ser—Lys—Gly-(7)

40
(8) Cys—Phe—Gly—Leu—Lys—Leu—Asp—Arg—Ile-(9)

50         53
(10) Gly—Ser—Met—Ser—Gly—Leu—Gly—Cys—OH
```

[where (1)/(2), (3)/(4), (5)/(6), (7)/(8) and (9)/(10) are respectively bonded directly, and each of the cysteine residues (Cys) at positions 37 and 53 form an intramolecular S-S bond]. (See SEQ ID NO. 1)

This peptide is hereinafter referred to as "CNP-53".

Figure 5:
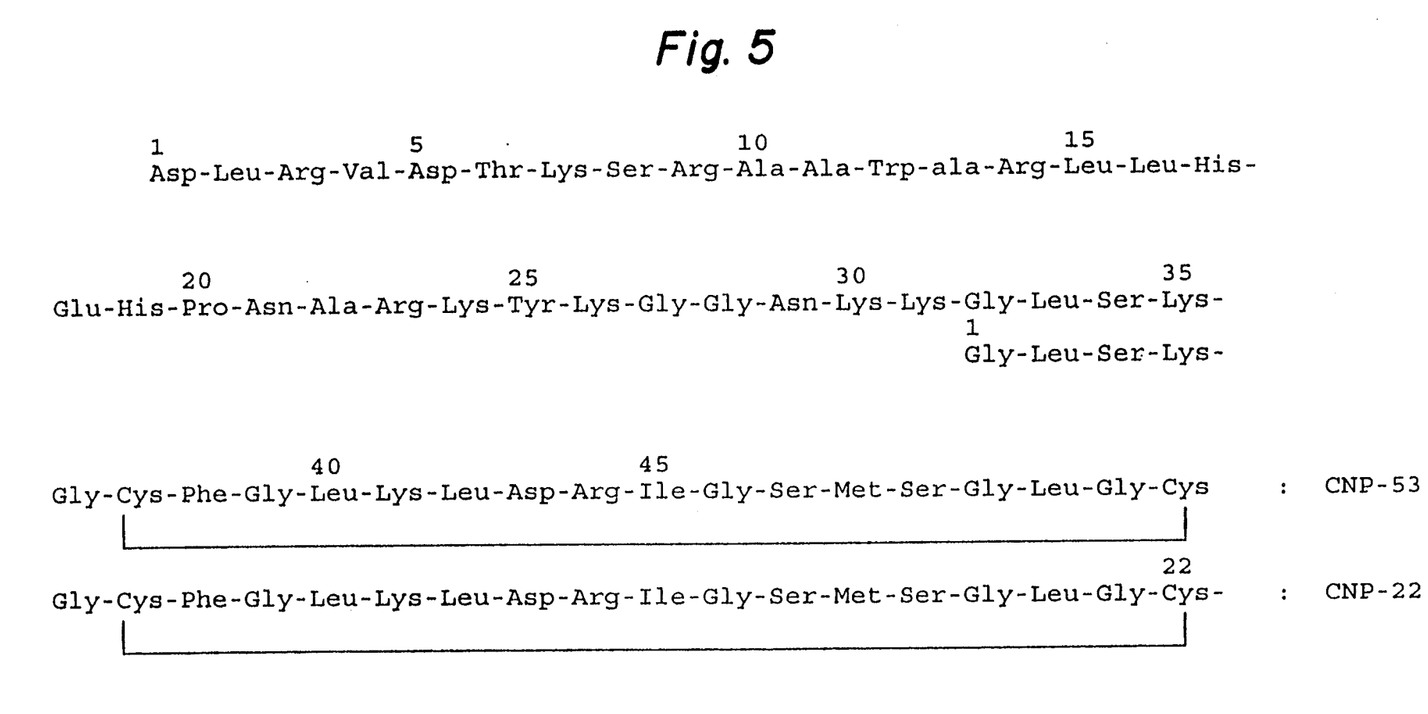
FIG. 5 is a chart showing the homology between the primary amino acid sequence of CNP-53 (see SEQ ID NO: 1) up to position 45 from the N-terminus and that of CNP-22 (See SEQ ID NO: 2)

As shown in FIG. 5, CNP-53 has in its C-terminal portion the same amino acid sequence as CNP-22. In other words, CNP-53 has 31 amino acid residues added to the N-terminus of the previously isolated and identified CNP-22. In addition, CNP-53 has a Lys-Lys sequence present in the immediate N-terminal portion of the area corresponding to CNP-22 (i.e., at positions 30 and 31 of CNP-53)—said Lys-Lys sequence is known to be a site for recognition and cleavage by processing enzymes in the case where the final peptide hormone is produced from the precursor protein in the biosynthesis of many peptide hormones; hence, CNP-53 which has been isolated and identified in accordance with the present invention may occur in porcine brain as a mere precursor peptide for CNP-22. However, as will be described later in the examples of the present invention, CNP-53 is present in porcine brain in a larger amount than CNP-22, so there is high possibility that CNP-53 as it occurs in the brain is present not only as a mere precursor peptide for CNP-22 but also as a hormone that is directly responsible for regulating the homeostatic balance of body fluid volume and blood pressure in the brain.

Among the 31 N-terminal amino acids of the peptide CNP-53, those which are basic are highly susceptible to processing with enzymes. Hence, several peptide derivatives would be produced with additional amino acids being attached to the N-terminus of CNP-22.

Such peptide derivatives include peptides represented by the following amino acid sequence: (See SEQ ID NO. 2)

```
       1                                    10
X—Gly—Leu—Ser—Lys—Gly—Lys—Phe—Gly—Leu—Lys-(1)

20
(2) Leu—Asp—Arg—Ile—Gly—Ser—Met—Ser—Gly—Leu-(3)

22
          (4) Gly—Cys—OH
```

[where (1)/(2) and (3)/(4) are respectively bonded directly; each of the cysteine residues (Cys) at positions 6 and 22 forms an intramolecular S-S bond; and X is a peptide represented by the following formula:

```
                        H—Vla—Asp—Thr—Lys—Ser—Arg-(1')
(2')Ala—Ala—Trp—Ala—Arg—Leu—Leu—His—Glu-(3')
(4')His—Pro—Asn—Ala—Arg—Lys—Tyr—Lys—Gly-(5')
(6')Gly—Asn—Lys—Lys—   (see SEQ ID NO: 3);

H—Ser—Arg-(1')
(2')Ala—Ala—Trp—Ala—Arg—Leu—Leu—His—Glu-(3')
(4')His—Pro—Asn—Ala—Arg—Lys—Tyr—Lys—Gly-(5')
(6')Gly—Asn—Lys—Lys—   (see SEQ ID NO: 4);

H—Ala—Ala—Trp—Ala—Arg—Leu—Leu—His—Glu-(3')
(4')His—Pro—Asn—Ala—Arg—Lys—Tyr—Lys—Gly-(5')
(6')Gly—Asn—Lys—Lys—   (see SEQ ID NO: 5);

H—Leu—Leu—His—Glu-(3')
(4')His—Pro—Asn—Ala—Arg—Lys—Tyr—Lys—Gly-(5')
(6')Gly—Asn—Lys—Lys—   (see SEQ ID NO: 6);

H—Tyr—Lys—Gly—Gly—Asn—Lys—Lys—
(see SEQ ID NO: 7);

or

H—Gly—Gly—Asn—Lys—Lys—   (see SEQ ID NO: 7)
```

(where (1')/(2'), (3')/(4') and (5')/(6') are respectively bonded directly)].

As described on the foregoing pages, the present inventors isolated and identified a novel peptide of the CNP family from porcine brain using as an indicator the performance of an RIA system that involved the use of an anti-CNP-22 antiserum and successfully purified a homogeneous and pure peptide that showed immunoreactivity with the anti-CNP-22 antiserum. By analyzing its structure, the present inventors found that the purified peptide was composed of 53 amino acid residues containing CNP-22 in the C-terminal portion and that it had diuretic and natriuretic actions. The present invention has been accomplished on the basis of these findings.

The following examples are provided for the purpose of further illustrating the present invention but are in no way to be taken as limiting.

EXAMPLE 1

Preparation of Anti-CNP-22 Antiserum and Construction of RIA System

A. Preparation of Anti-CNP-22 Antiserum

Six milligrams of chemically synthesized CNP-22 and 15 mg of bovine thyroglobulin (product of Sigma Co.) were dissolved in 2 ml of 0.1M phosphate buffer (pH 7.4). To the solution, 100 μl of 5% glutaraldehyde was added and the mixture was agitated at 0° C. for 20 min to have CNP-22 bound to the thyroglobulin. Then, the solution was dialyzed five times against water (500 ml) and twice against 500 ml of 50 mM phosphate buffer (pH 7.4) containing 80 mM NaCl, whereby excess salts and reagents were removed from the reaction solution. Subsequently, 50 mM phosphate buffer containing 80 mM NaCl was added to the reaction solution to make a total volume of 12 ml. Thereafter, an equal volume of Freund's complete adjuvant was added to form an emulsion. A rabbit (New Zealand White) was repeatedly immunized with the emulsion at 20-day intervals so as to prepare an anti-CNP-22 antiserum. The thus prepared antiserum was named "#171-4".

B. Construction of RIA System

In the first step, [Tyr°] CNP-22 [a peptide having a tyrosine residue (Tyr) added to the N-terminus of CNP-22] was chemically synthesized. Then, $I^{125}$ was introduced into the N-terminal Tyr residue by the method of Miyata et al. (Miyata, A. et al., Biochem. Biophys. Res. Commun., 129, 248–255, 1985) and the $I^{125}$ labelled monoiodo(Tyr°) CNP-22 was separated and isolated by reverse-phase HPLC.

In the next step, an RIA system was constructed by the following method using the thus I125 labelled [Tyr°] CNP-22 and the antibody (#171-4) prepared in Example 1-A.

As a buffer for the RIA system, 50 mM phosphate buffer (pH 7.4) containing 80 mM NaCl, 0.1% Triton X-100, 25 mM EDTA, 0.05% $NaN_3$, 3.1% dextran T-40 and 0.25% BSA (as treated with N-ethylmaleimide) was used. A standard CNP-22 solution or assay sample (100 μl) and the antibody #171-4 prepared in Example 1-A (100 μl of a 60,000-fold dilution) were added to the buffer and the mixture was subjected to reaction at 4° C. for 24 h. Thereafter, 100 μl of a tracer ($I^{125}$ labelled [Tyr°] CNP-22) was added and reaction was performed at 4° C. for 36 h. Thereafter, polyethylene glycol was added and the radioactivity of the resulting precipitate was measured with a gamma-counter (ARC-600 of Aloka Co.).

Using this RIA system, CNP-22 could be measured in amounts of 1–100 fmol/tube; antibody #171-4 was found to have 0.015% and 0.46% cross-reactivities with α-ANP and pBNP-26, respectively.

EXAMPLE 2

Isolation and Purification of CNP-53

Forty kilograms of brain was extracted from 480 swines, shreded and had the protease inactivated by treatment with 2 volumes of boiling water for 5 min. After cooling, glacial acetic acid was added to give a final concentration of 1M. The thus treated tissue was homogenized with a Polytron mixer. Subsequently, the homogenate was centrifuged to be divided into a precipitate fraction and a supernatant fraction, which was concentrated with a pellicon cassette (PCAC #000-05, Millipore). Acetone was added to the concentrate (final concentration, 66%) and the resulting precipitate was removed by centrifugation, with the supernatant being subsequently concentrated under vacuum. The resulting concentrate was dissolved in 0.5M acetic acid and the solution was loaded onto a C-18 silica gel column (capacity, 1.5 9,; LC-SORB SPW-CODS, Chemco) in four divided portions. The peptides adsorbed on the column were eluted with a solution prepared from water, acetonitrile (CHSCN) and 10% trifluoroacetic acid (TFA) in a ratio of 40:60:1 (v/v). By concentrating the eluate, a residue containing peptides in a dry weight of 26 g was obtained. One half the amount of this residue was dissolved in 1M acetic acid and subjected to ion-exchange chromatography on an SP-Sephadex C-25 column ($H^+$-form, 3×38 cm) equilibrated with 1M acetic acid. The peptides adsorbed on the column were successively eluted with 1M acetic acid, 2M pyridine and 2M pyridine-acetic acid (pH 5.0) in the order written. The thus obtained fractions were designated SP-I, SP-II and SP-III, respectively, and lyophilized. To purify CNP-53 of the present invention, fraction SP-III was used as a starting material. Almost all of the peptides that exhibited immunoreactivity with the anti-CNP-22 antiserum in the RIA system described in Example 1 were found to be contained in fraction SP-III.

In the first place, fraction SP-III (dry weight, 5.2 g) was subjected to gel filtration on a Sephadex G-50 column (fine, 7.5×145 cm, Pharmacia). whereby fractions containing peptide with molecular weights of ca. 1000–5000 were obtained in a dry weight of 2.96 g. Half (1.48 g) of those fractions was further fractionated on a Sephadex G-25 column (fine, 7.5×150 cm, Pharmacia) and the immunoreactivity of each eluted fraction with the anti-CNP-22 antiserum was examined with the RIA system described in Example 1.

Figure 1:
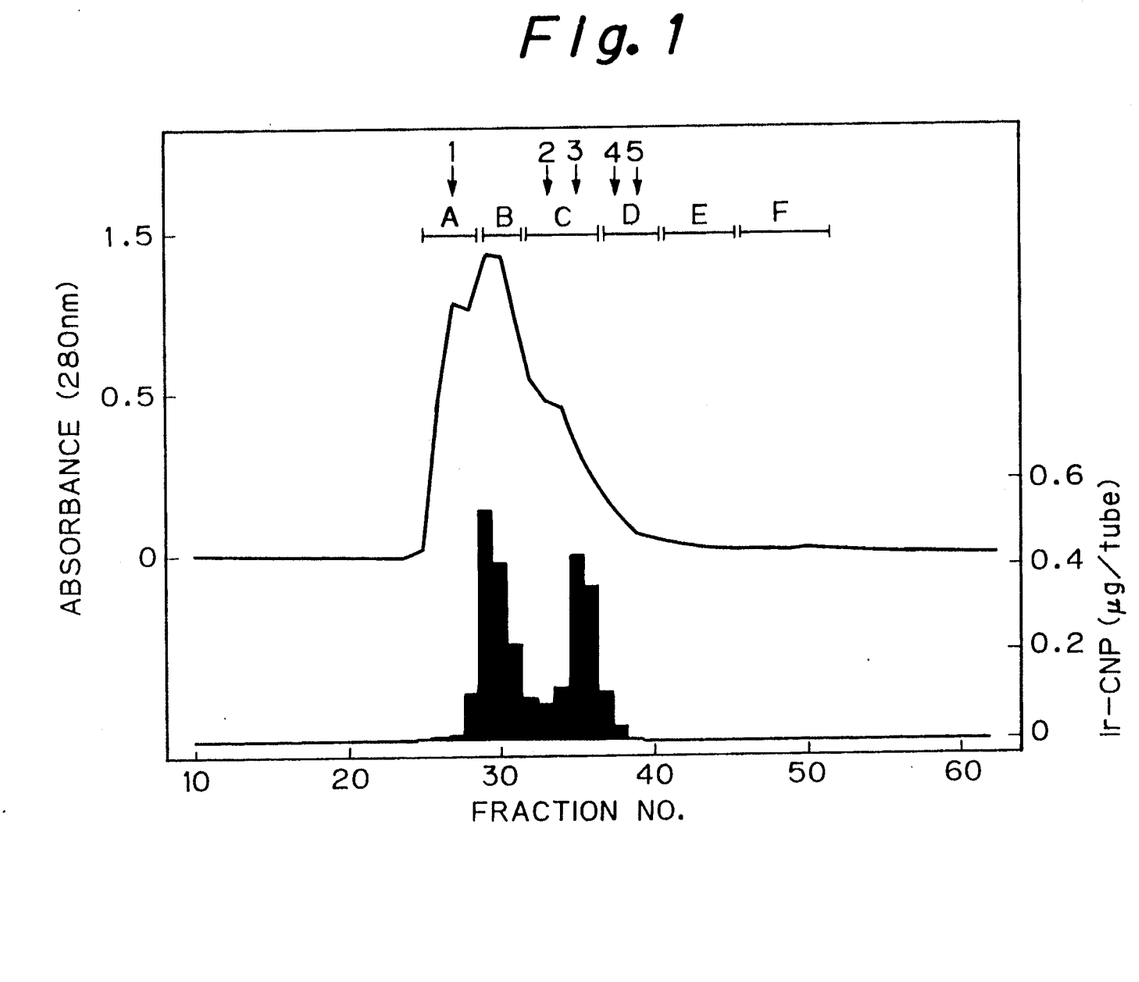
FIG. 1 is a chart showing the elution profile of purification on Sephadex G-25 of an extract from porcine brain (i.e., peptide fractions of molecular weights of ca. 1000–5000 that were obtained by fractionating SP-III fractions on Sephadex G-50), as well as the immunoreactivity of the resulting fractions with an anti-CNP-22 antiserum.

As shown in FIG. 1, two fractions exhibited immunoreactivity with the anti-CNP-22 antiserum (fraction B with molecular weight of ca. 4000–5000 and fraction C with molecular weight of ca. 2000–3000), and the ration of occurrence of peptide that reacted with the anti-CNP-22 antiserum was ca. 4:3 in fractions B and C. In FIG. 1, arrows 1–5 indicate the positions of elution of bovine serum albumin, BNP2, BNP26, α-ANP (4–28) and neurotension, respectively, on the column. It is known that CNP-22 which was already isolated and identified by the present inventors is contained in fraction C. In the present invention, fraction B was further purified by the following procedure.

First, fraction B (dry weight, 740 mg) having molecular weights of ca. 4000–5000 was further fractionated by CM (CM-52, 2.4×52.3 cm, Whatman) ion-exchange chromato- graphy (eluting solution A: 10 mM $HCOONH_4$ (PH 6.6)/$CH_3CN$=90/10 (V/V); eluting solution B: 0.6M $HCOONH_4$ (pH 6.6)/$CH_3CN$=90/10

(V/V); eluting condition: linear density gradient using eluting solutions A and B; flow rate: 40 ml/h; fraction size: 20 ml/tube) and each of the resulting eluted fractions was measured for its immunoreactivity with the anti-CNP-22 antiserum.

Figure 2:
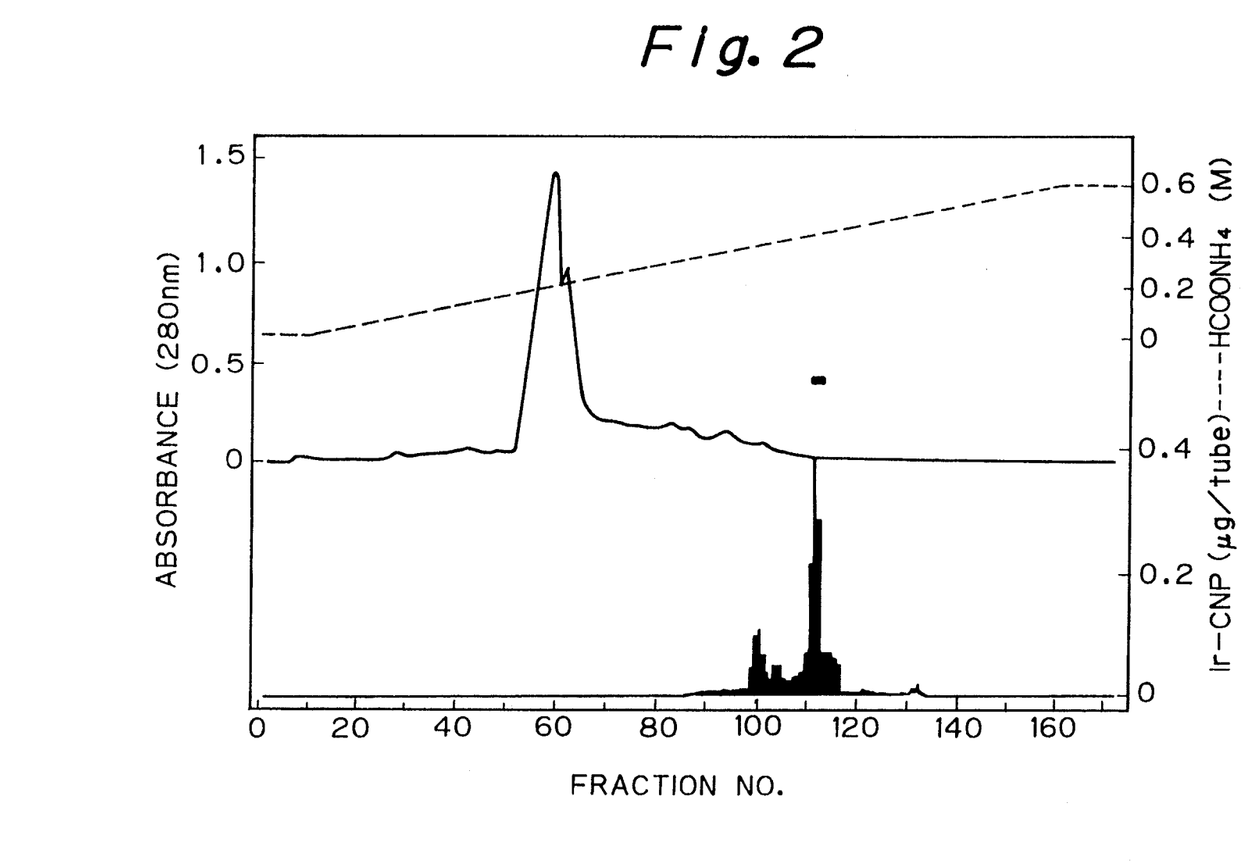
FIG. 2 is a chart showing the elution profile of purification of fractions B in FIG. 1 by ion-exchange chromatography on CM-52, as well as the immunoreactivity of the resulting fractions with an anti-CNP-22 antiserum.

As shown in FIG. 2, immunoreactivity with the anti-CNP-22 antiserum was found in fractions #99-102 and 111-113, which were collected and lyophilized. Subsequently, fractions #111-113 (dry weight, 8.5 mg) obtained by the CM-52 chromatography were subjected to immunoaffinity chromatography using an anti-ANP antibody (details of column preparation are described in the following report by the present inventors: Ueda, S. et al., Biochem. Biophys. Res. Commun., 149, 1055-1062, 1987) and the peptides adsorbed on the column were eluted with a 1M acetic acid solution containing 10% CH$_3$CN. The eluted fractions were separated and purified by reverse-phase HPLC (flow rate: 1.5 ml/min; eluting solution A: H$_2$O/CH$_3$CN/10% TFA=90/10/1 (V/V); eluting solution B. H$_2$O/CH$_3$CN/10% TFA=40/60/1 (V/V); eluting condition: linear density gradient using eluting solutions A and B; eluting time: 120 min) using a C-18 column (Hi-Pore RP-318, 4.6×250 mm, Bio-Rad), and the resulting eluted fractions were examined for their immunoreactivity with the anti-CNP-22 antiserum.

Figure 3A:
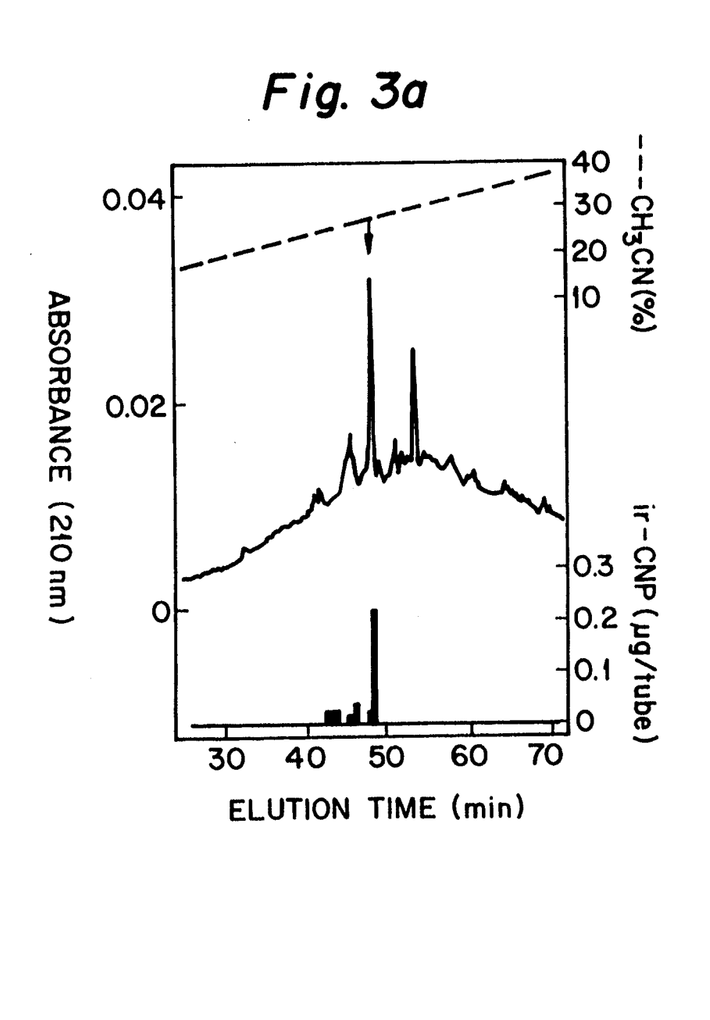
FIG. 3a and FIG. 3b are charts showing the elution profile of reverse-phase HPLC used for final purification of CNP-53, as well as the immunoreactivity of the resulting fractions with an anti-CNP-22 antiserum.
Figure 3B:
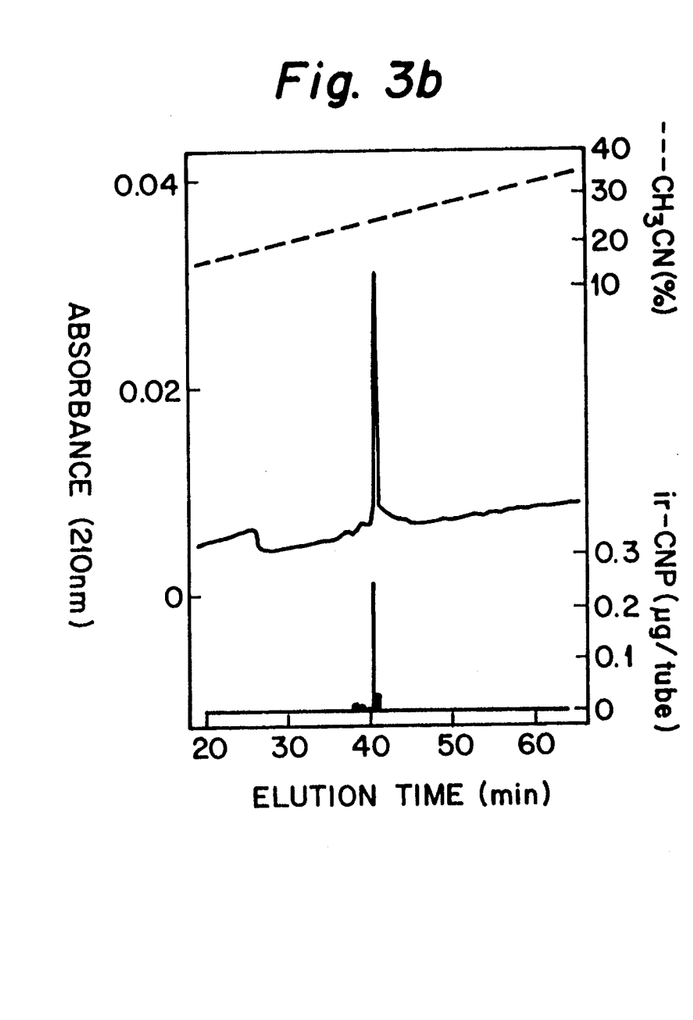

As a result, a fraction that had immunoreactivity with the anti-CNP-22 antiserum and that showed maximum uv absorption at 210 nm was obtained in the position indicated by arrow in FIG. 3a.

In order to achieve final purification of the novel peptide (CNP-53) of the present invention, the fraction obtained by the previous C-18 column chromatography (as indicated by arrow in FIG. 3a) was separated and purified by reverse-phase HPLC (flow rate: 1 ml/min; eluting solution A: H$_2$O/CH$_3$CN/10% TFA-90/10/1 (V/V); eluting solution B: H$_2$O/CH$_3$CN/10% TFA=40/60/1 (V/V); eluting condition: linear density gradient using eluting solutions A and B; eluting time: 120 min) using a diphenyl column (219 TP54, 4.6×250 mm, Vydac) and the resulting eluted fractions were examined for their immunoreactivity with the anti-CNP-22 antiserum.

As shown in FIG. 3b, a peptide showing immunoreactivity with the anti-CNP-22 antiserum could successfully be purified to homogeneity (showing a single peak) and it was designated "CNP-53".

The yield of CNP-53 as obtained by the purification method employed in the present invention was ca. 130 pmol (700 ng) from 40 kg of porcine brain.

EXAMPLE 3

Determining the Structure of CNP-53

A. Analyzing the Primary Amino Acid Sequence of CNP-53

Three fourths (ca. 525 ng) of the CNP-53 obtained in Example 2 were loaded in an automatic amino acid sequencer (Applied Biosystems 470A/120A) and the primary amino acid sequence was analyzed by Edman degradation. The results were as shown in FIG. 4a and b, from which it was concluded that the amino acids in the 45 N-terminal positions of CNP-53 had the following primary sequence. However, the PTH-amino acid at cycle 37 was undetectable by the analysis described above, so the present inventors identified that amino acid as a cysteine residue:

1
H—Asp—Leu—Arg—Val—Asp—Thr—Lys—Ser—Arg-(1)

10
(2)Ala—Ala—Trp—Ala—Arg—Leu—Leu—His—Glu-(3)

20
(4)His—Pro—Asn—Ala—Arg—Lys—Tyr—Lys—Gly-(5)

30
(6)Gly—Asn—Lys—Lys—Gly—Leu—Ser—Lys—Gly-(7)

40              45
(8)Cys—Phe—Gly—Leu—Lys—Leu—Asp—Arg—Ile ...

[where (1)/(2), (3)/(4), (5)/(6) and (7)/(8) are respectively bonded directly] (See SEQ ID NO. 9).

In the analysis described above, PTH-amino acid was detectable but unidentifiable beyond 45 cycles.

B. Homology in Primary Amino Acid Sequence Between the N-terminus of CNP-53 and CNP-22

The primary sequence of the 45 N-terminal amino acids in CNP-53 as determined in Example 3-A was compared with the previously identified primary amino acid sequence of CNP-22. As shown in FIG. 5, the primary sequence of amino acids in CNP-53 at positions 32-45 was completely identical to the primary sequence of the 14 N-terminal amino acids in CNP-22.

C. Chick Rectum Relaxant Activity of CNP-53

The chick rectum relaxant activity of CNP-53 was measured in accordance with the method of Currie et al. (Currie et al., Nature, 221, 1-13, 1983). When measured with the assay system proposed by Currie et al., CNP-53 showed a comparable chick rectum relaxant activity to CNP-22.

D. Immunoreactivity of CNP-53 with Anti-CNP-22 Antiserum

Using the RIA system constructed in Example 1, the immunoreactivity per molecule of CNP-53 with the anti-CNP-22 antiserum was determined, assuming that CNP-53 was a peptide composed of 53 amino acid residues containing CNP-22 at the C-terminus. The activity level of CNP-53 was comparable to that of CNP-22.

Based on the results of analyses described above, the present inventors concluded that CNP-53 was a novel peptide represented by the following primary amino acid sequence:

1
H—Asp—Leu—Arg—Val—Asp—Thr—Lys—Ser—Arg-(1)

10
(2) Ala—Ala—Trp—Ala—Arg—Leu—Leu—His—Glu-(3)

20
(4) His—Pro—Asn—Ala—Arg—Lys—Tyr—Lys—Gly-(5)

30
(6) Gly—Asn—Lys—Lys—Gly—Leu—Ser—Lys—Gly-(7)

40
(8) Cys—Phe—Gly—Leu—Lys—Leu—Asp—Arg—Ile-(9)

50              53
(10) Gly—Ser—Met—Ser—Gly—Leu—Gly—Cys—OH

[where (1)/(2), (3)/(4), (3)/(6), (7)/(8) and (9)/(10) are respectively bonded directly, and each of the cysteine residues (Cys) at positions 37 and 53 forms an intramolecular S-S bond] (see SEQ ID NO: 1).

As described on the foregoing pages, the present inventors first prepared an antibody that specifically recognized the structure of the previously isolated and identified CNP-22 and then constructed an RIA system using that antibody. Subsequently, with the performance of this RIA system used as an indicator, the present inventors searched for a novel peptide in porcine brain that could be assigned to the CNP family as was CNP-22. As a result, they successfully isolated a homogeneous and pure novel peptide (CNP-53) that obviously differed from CNP-22.

By subsequent structural analysis of this peptide, the present inventors identified CNP-53 as a peptide composed of 53 amino acid residues containing CNP-22 at the C-terminus and found that it was a novel peptide classifiable in the CNP family.

With the structure of CNP-53 having been identified by the present invention, it will be possible in the future to obtain CNP-53 in large quantities by either chemical synthesis or gene manipulation and it is expected that the physiological actions of CNP-53 in vivo can be unravelled by carrying out various pharmacological tests. In the primary amino acid sequence of CNP-53 shown in FIG. 5, five lysine (Lys) residues and four arginine (Arg) residues are present between positions 1 and 32 (Lys at positions 7, 24, 26, 30 and 31, and Arg at positions 3, 9, 14 and 23), so there is high likelihood that CNP-53 is cleaved specifically in vivo at the C-terminus of any one of those basic amino acid residues with processing enzymes so as to be converted not only to CNP-22 but also to various peptides having additional amino acids attached to the N-terminus of CNP-22 (including, for example, those peptides which correspond to positions 4–53, 8–53, 10–53, 15–53, 25–53 and 27–52 in the primary amino acid sequence shown in FIG. 5), which peptides have high possibility to show different physiological activities in vivo than CNP-53 and CNP-22. Since the structure of CNP-53 has been identified by the present invention, the possibilities described above can be verified by performing various pharmacological tests with those peptides prepared by either chemical synthesis or gene manipulation. Furthermore, if a DNA probe that corresponds to CNP-53 is prepared on the basis of information on its primary amino acid sequence and if it is used to isolate and analyze the gene and cDNA that codes for CNP-53, the structures of precursor proteins of CNP-22 and CNP-53 can be identified. Hence, in view of the above facts, the present invention will make great contributions not only to future studies for unravelling the mechanism behind the biosynthesis of peptides of the CNP family and their distribution in vivo and physiological actions, but also to the efforts to develop those peptides of the CNP family as pharmaceuticals.

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
        ( A ) LENGTH: 53 amino acids
        ( B ) TYPE: amino acid
        ( C ) STRANDEDNESS: single
        ( D ) TOPOLOGY: linear     ( i i ) MOLECULE TYPE: protein     ( x i ) SEQUENCE DESCRIPTION: SEQ ID NO:1:

```
Asp Leu Arg Val Asp Thr Lys Ser Arg Ala Ala Trp Ala Arg Leu Leu
 1               5                  10                      15

His Glu His Pro Asn Ala Arg Lys Tyr Lys Gly Gly Asn Lys Lys Gly
                20                  25                  30

Leu Ser Lys Gly Cys Phe Gly Leu Lys Leu Asp Arg Ile Gly Ser Met
            35                  40                  45

Ser Gly Leu Gly Cys
        50
```

( 2 ) INFORMATION FOR SEQ ID NO:2:

( i ) SEQUENCE CHARACTERISTICS:
        ( A ) LENGTH: 22 amino acids
        ( B ) TYPE: amino acid
        ( C ) STRANDEDNESS: single
        ( D ) TOPOLOGY: linear     ( i i ) MOLECULE TYPE: protein     ( x i ) SEQUENCE DESCRIPTION: SEQ ID NO:2:

```
Gly Leu Ser Lys Gly Cys Phe Gly Leu Lys Leu Asp Arg Ile Gly Ser
 1               5                  10                      15

Met Ser Gly Leu Gly Cys
```

20

(2) INFORMATION FOR SEQ ID NO:3:

(i) SEQUENCE CHARACTERISTICS:
        (A) LENGTH: 28 amino acids
        (B) TYPE: amino acid
        (C) STRANDEDNESS: single
        (D) TOPOLOGY: linear     (ii) MOLECULE TYPE: protein     (xi) SEQUENCE DESCRIPTION: SEQ ID NO:3:

```
Val Asp Thr Lys Ser Arg Ala Ala Trp Ala Arg Leu Leu His Glu His
 1               5                  10                  15
Pro Asn Ala Arg Lys Tyr Lys Gly Gly Asn Lys Lys
            20                  25
```

(2) INFORMATION FOR SEQ ID NO:4:

(i) SEQUENCE CHARACTERISTICS:
        (A) LENGTH: 24 amino acids
        (B) TYPE: amino acid
        (C) STRANDEDNESS: single
        (D) TOPOLOGY: linear     (ii) MOLECULE TYPE: protein     (xi) SEQUENCE DESCRIPTION: SEQ ID NO:4:

```
Ser Arg Ala Ala Trp Ala Arg Leu Leu His Glu His Pro Asn Ala Arg
 1               5                  10                  15
Lys Tyr Lys Gly Gly Asn Lys Lys
            20
```

(2) INFORMATION FOR SEQ ID NO:5:

(i) SEQUENCE CHARACTERISTICS:
        (A) LENGTH: 22 amino acids
        (B) TYPE: amino acid
        (C) STRANDEDNESS: single
        (D) TOPOLOGY: linear     (ii) MOLECULE TYPE: protein     (xi) SEQUENCE DESCRIPTION: SEQ ID NO:5:

```
Ala Ala Trp Ala Arg Leu Leu His Glu His Pro Asn Ala Arg Lys Tyr
 1               5                  10                  15
Lys Gly Gly Asn Lys Lys
            20
```

(2) INFORMATION FOR SEQ ID NO:6:

(i) SEQUENCE CHARACTERISTICS:
        (A) LENGTH: 17 amino acids
        (B) TYPE: amino acid
        (C) STRANDEDNESS: single
        (D) TOPOLOGY: linear     (ii) MOLECULE TYPE: protein     (xi) SEQUENCE DESCRIPTION: SEQ ID NO:6:

```
Leu Leu His Glu His Pro Asn Ala Arg Lys Tyr Lys Gly Gly Asn Lys
 1               5                  10                  15
Lys
```

(2) INFORMATION FOR SEQ ID NO:7:

(i) SEQUENCE CHARACTERISTICS:
        (A) LENGTH: 7 amino acids (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:7:

Tyr  Lys  Gly  Gly  Asn  Lys  Lys
    1                   5

(2) INFORMATION FOR SEQ ID NO:8:

(i) SEQUENCE CHARACTERISTICS:
            (A) LENGTH: 5 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:8:

Gly  Gly  Asn  Lys  Lys
    1              5

(2) INFORMATION FOR SEQ ID NO:9:

(i) SEQUENCE CHARACTERISTICS:
            (A) LENGTH: 45 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO:9:

Asp  Leu  Arg  Val  Asp  Thr  Lys  Ser  Arg  Ala  Ala  Trp  Ala  Arg  Leu  Leu
    1                   5                        10                            15

His  Glu  His  Pro  Asn  Ala  Arg  Lys  Tyr  Lys  Gly  Gly  Asn  Lys  Lys  Gly
                        20                        25                       30

Leu  Ser  Lys  Gly  Cys  Phe  Gly  Leu  Lys  Leu  Asp  Arg  Ile
                   35                        40                   45

(2) INFORMATION FOR SEQ ID NO:10:

(i) SEQUENCE CHARACTERISTICS:
            (A) LENGTH: 53 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO:10:

Asp  Leu  Arg  Val  Asp  Thr  Lys  Ser  Arg  Ala  Ala  Trp  Ala  Arg  Leu  Leu
    1                   5                        10                            15

His  Glu  His  Pro  Asn  Ala  Arg  Lys  Tyr  Lys  Gly  Gly  Asn  Lys  Lys  Gly
                        20                        25                       30

Leu  Ser  Lys  Gly  Cys  Phe  Gly  Leu  Lys  Leu  Asp  Arg  Ile  Gly  Ser  Met
                   35                        40                   45

Ser  Gly  Leu  Gly  Cys
              50

(2) INFORMATION FOR SEQ ID NO:11:

(i) SEQUENCE CHARACTERISTICS:
            (A) LENGTH: 22 amino acids
            (B) TYPE: amino acid
            (C) STRANDEDNESS: single
            (D) TOPOLOGY: linear (i i) MOLECULE TYPE: protein (x i) SEQUENCE DESCRIPTION: SEQ ID NO:11:

Gly Leu Ser Lys Gly Cys Phe Gly Leu Lys Leu Asp Arg Ile Gly Ser
1               5                   10                  15

Met Ser Gly Leu Gly Cys
            20

(2) INFORMATION FOR SEQ ID NO:12:

(i) SEQUENCE CHARACTERISTICS:
      (A) LENGTH: 549 base pairs
      (B) TYPE: nucleic acid
      (C) STRANDEDNESS: double
      (D) TOPOLOGY: linear (i i) MOLECULE TYPE: DNA (genomic)

(x i) SEQUENCE DESCRIPTION: SEQ ID NO:12:

| | | | | | | |
|---|---|---|---|---|---|---|
| GCACCCAGCC | GGCGCCGCGC | AGCACTGGGA | CTCGCGCCCG | CACCGCAGCC | CGGCCAGTCT | 60 |
| GCTCCGCGCT | CGCTTGCCAG | TCTGCCCGCC | GGCCCCGTGC | ACCTCTCTGC | CGCCGATCTG | 120 |
| CGCCCCTCCA | CCCCACAGGC | ACCATGCACC | TCTCCAGCT | GCTGGCCTGC | GCTCTGCTGC | 180 |
| TCACGCTCCT | CTCGCTCCGG | CCCTCCGAAG | CCAAGCCCGG | AGCGCCGCCG | AAGGTCCCTC | 240 |
| GAACTCCGCC | AGGGGAGGAG | GTGGCCGAGC | CCAGGCTGC | GGGCGGCGGT | CAGAAGAAGG | 300 |
| GCGACAAGAC | TCCTGGGGGC | GGTGGCGCCA | ACCTCAAGGG | CGACCGGTCT | CGACTGCTCC | 360 |
| GGGACCTGCG | CGTGGACACC | AAGTCTCGGG | CGGCGTGGGC | CCGCCTTCTG | CACGAGCACC | 420 |
| CCAACGCGCG | CAAATACAAA | GGAGGCAACA | AGAAGGGTTT | GTCCAAGGGC | TGCTTCGGCC | 480 |
| TCAAACTGGA | CCGGATCGGC | TCCATGAGCG | GCCTGGGATG | TTAGTGCGGC | GACCCCTGGC | 540 |
| GGCGGTGAG | | | | | | 549 |

What is claimed is:

1. An isolated peptide represented by the following amino acid sequence:

1
H—Asp—Leu—Arg—Val—Asp—Thr—Lys—Ser—Arg-(1)

10
(2) Ala—Ala—Trp—Ala—Arg—Leu—Leu—His—Glu-(3)

20
(4) His—Pro—Asn—Ala—Arg—Lys—Tyr—Lys—Gly-(5)

30
(6) Gly—Asn—Lys—Lys—Gly—Leu—Ser—Lys—Gly-(7)

40
(8) Cys—Phe—Gly—Leu—Lys—Leu—Asp—Arg—Ile-(9)

50        53
(10) Gly—Ser—Met—Ser—Gly—Leu—Gly—Cys—OH where (1)/(2), (3)/(4), (5)/(6), (7)/(8) and (9)/(10) are respectively bonded directly, and each of the cysteine residues (Cys) at positions 37 and 53 forms an intramolecular S-S bond (see SEQ ID NO. 1).

2. An isolated peptide represented by the following amino acid sequence:

1                              10
X—Gly—Leu—Ser—Lys—Gly—Cys—Phe—Gly—Leu—Lys-(1)

20
(2) Leu—Asp—Arg—Ile—Gly—Ser—Met—Ser—Gly—Leu-(3)

22
(4) Gly—Cys—OH(see SEQ ID NO: 2)

where (1)/(2) and (3)/(4) are respectively bonded directly; each of the cysteine residues (Cys) at positions 6 and 22 forms an intramolecular S-S bond; and X is selected from the group consisting of peptides represented by the following formula:

H—Vla—Asp—Thr—Lys—Ser—Arg-(1')
(2')Ala—Ala—Trp—Ala—Arg—Leu—Leu—His—Glu-(3')
(4')His—Pro—Asn—Ala—Arg—Lys—Tyr—Lys—Gly-(5')
(6')Gly—Asn—Lys—Lys—;

H—Ser—Arg-(1')
(2')Ala—Ala—Trp—Ala—Arg—Leu—Leu—His—Glu-(3')
(4')His—Pro—Asn—Ala—Arg—Lys—Tyr—Lys—Gly-(5')
(6')Gly—Asn—Lys—Lys—;

H—Ala—Ala—Trp—Ala—Arg—Leu—Leu—His—Glu-(3')
(4')His—Pro—Asn—Ala—Arg—Lys—Tyr—Lys—Gly-(5')
(6')Gly—Asn—Lys—Lys—;

H—Leu—Leu—His—Glu-(3')
(4')His—Pro—Asn—Ala—Arg—Lys—Tyr—Lys—Gly-(5')
(6')Gly—Asn—Lys—Lys—;

H—Tyr—Lys—Gly—Gly—Asn—Lys—Lys—;

and

H—Gly—Gly—Asn—Lys—Lys— where (1')/(2'), (3')/(4') and (5')/(6') are respectively bonded directly.

* * * * *